United States Patent [19]

Siegle et al.

[11] 4,008,328
[45] Feb. 15, 1977

[54] N-METHYL-N-(3-TRIFLUOROMETHYL-PHENYLSULFENYL)-CARBONYLOXIME-CARBAMATES

[75] Inventors: Peter Siegle, Cologne; Engelbert Kühle, Bergisch-Gladbach; Ingeborg Hammann, Cologne; Wolfgang Behrenz, Overath-Steinenbruck; Bernhard Homeyer, Opladen, all of Germany

[73] Assignee: Bayer Aktiengesellschaft, Leverkusen, Germany

[22] Filed: Feb. 24, 1975

[21] Appl. No.: 552,502

[30] Foreign Application Priority Data

Feb. 27, 1974  Germany ..................... 2409463

[52] U.S. Cl. ................. 424/298; 424/308; 260/453 RW; 260/470; 260/327 M
[51] Int. Cl.² ............... A01N 9/00; C07C 83/08
[58] Field of Search ........... 260/566 AC, 453 RW, 260/470; 424/298

[56] References Cited

UNITED STATES PATENTS 3,890,386  6/1975  Kuhle et al. ............. 260/566 AC

FOREIGN PATENTS OR APPLICATIONS 2,147,850  8/1974  Germany ................... 260/453 RW

*Primary Examiner*—Lewis Gotts
*Assistant Examiner*—D. R. Phillips
*Attorney, Agent, or Firm*—Burgess, Dinklage & Sprung

[57] ABSTRACT

N-methyl-N-(3-trifluoromethylphenylsulfenyl)-carbonyloxime-carbamates of the formula

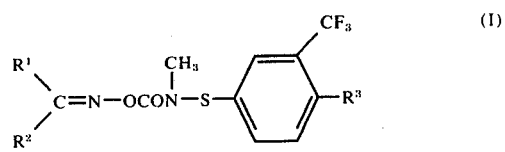

in which
R¹ and R² each independently is hydrogen, alkyl, alkenyl, alkynyl, alkoxy, alkylthio, alkoxycarbonyl, aminocarbonyl or alkylthioalkyl, or together are

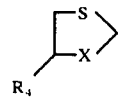

R₃ is hydrogen or halogen,
R₄ is hydrogen or C₁-C₄ alkyl, and
X is oxygen or sulfur, which possess insecticidal, acaricidal, nematicidal, fungicidal and bactericidal properties.

8 Claims, No Drawings

N-METHYL-N-(3-TRIFLUOROMETHYLPHENYL-SULFENYL)-CARBONYLOXIME-CARBAMATES

The present invention relates to and has for its objects the provision of particular new N-methyl-N-(3-trifluoromethylphenylsulfenyl)-carbonyloxime-carbamates which possess insecticidal, acaricidal, nematicidal, fungicidal and bactericidal properties, active compositions in the form of mixtures of such compounds with solid and liquid dispersible carrier vehicles, and methods for producing such compounds and for using such compounds in a new way especially for combating pests, e.g. insects, acarids, nematodes, fungi and bacteria, with other and further objects becoming apparent from a study of the within specification and accompanying examples.

It has been disclosed in Belgian Pat. No. 674,792 that certain carbamic acid derivatives of oximes are good insecticides. Thus, for example, the N-methyl-carbamate of 1-methylthio-aldoxime (Compound A) is marketed under the trade name "Lannate". However, a disadvantage of these compounds is the very high toxicity to warm-blooded animals.

It has also been disclosed in German Published Specification DOS 2,147,850 that certain N-sulfenylated carbamic acid derivatives of oximes exhibit insecticidal effects. However, a disadvantage is that their activity is not always satisfactory if low amounts are used.

The present invention provides, as new compounds, the N-sulfenylated oxime-carbamates of the general formula

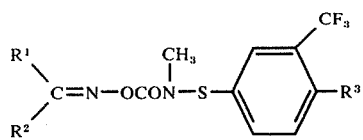  (I)

in which
R$^1$ and R$^2$ each independently is hydrogen, alkyl, alkenyl, alkynyl, alkoxy, alkylthio, alkoxycarbonyl, aminocarbonyl or alkylthioalkyl, or together are

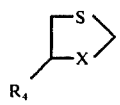

R$_3$ is hydrogen or halogen,
R$_4$ is hydrogen or C$_1$–C$_4$ alkyl, and
X is oxygen or sulfur.

The compounds of the formula (I) display strong insecticidal, acaricidal and nematicidal properties.

Preferably R$^1$ is hydrogen, straight-shain or branched lower alkyl with 1–4 carbon atoms (especially methyl), lower alkylthio with 1–4 carbon atoms (especially methylmercapto or butyl-mercapto), lower alkoxycarbonyl with 1–4 carbon atoms in the alkyl moiety, di-lower alkyl-aminocarbonyl with 1–4 carbon atoms in each alkyl moiety, or lower alkyl-thio-lower alkyl with up to 4 carbon atoms in each alkyl moiety, and R$_2$ is lower alkylthio with 1–4 carbon atoms or lower alkylthio-lower alkyl with 1–4 carbon atoms in each alkyl moiety, or R$^1$ and R$^2$ together are

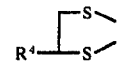

and
R$^4$ is hydrogen or methyl.

The invention also provides a process for the preparation of a compound of the formula (I) in which
a. a substituted carbamic acid fluoride of the general formula

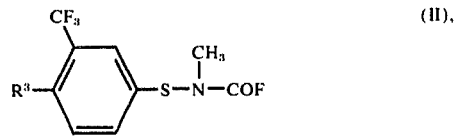  (II), in which
R$^3$ has the above-mentioned meaning,
is reacted, optionally in the presence of a diluent, with a compound of the general formula

  (III), in which
R$^1$ and R$^2$ have the above-mentioned meanings, the latter being reacted as such, optionally in the presence of an acid-binding agent, or in the form of an alkali metal salt thereof, or
b. a sulfenyl chloride of the general formula

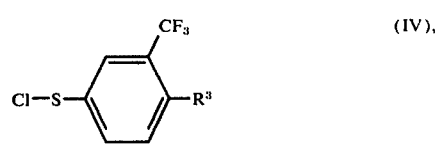  (IV), in which
R$^3$ has the above-mentioned meaning,
is reacted with a carbamate of the general formula

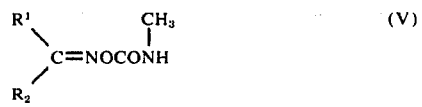  (V)

optionally in the presence of a diluent and of an acid-binding agent.

If N-methyl-N-(3-trifluoromethylphenyl sulfenyl)-carbamic acid fluoride and 1-methylthioacetaldoxime are used as starting materials in process variant (a), the reaction can be represented by the following equation:

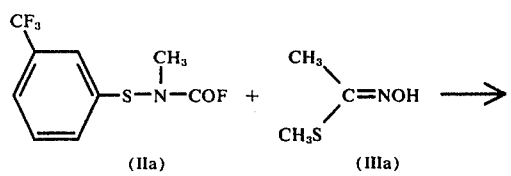
(IIa)  (IIIa)

-continued

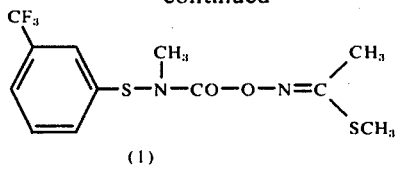

(1)

If, 1,3-dithiolane-2-oximino-N-methylcarbamate and 3-trifluoromethylphenyl sulfenyl chloride are used as starting materials in process variant (b), the reaction can be represented by the following equation:

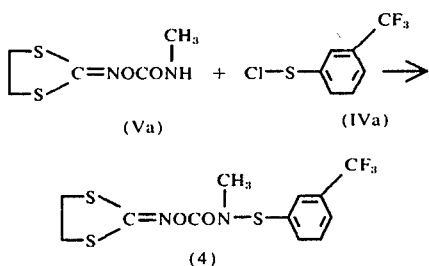

The starting materials required to prepare the compounds according to the invention are known.

Thus, the substituted carbamic acid fluorides of the formula (II) can be prepared according to a known process by reacting the corresponding known 3-trifluoromethylphenylsulfenyl chlorides of the formula (IV) with N-methylcarbamic acid fluoride according to German Published Specification DAS 1,297,095). Preferably, 3-trifluoromethylphenylsulfenyl chloride and 4-chloro-3-trifluoromethylsulfenyl chloride are used.

The oximes of the formula (III) which serve as the starting material can be obtained according to the process of U.S. Pat. No. 3,183,148, German Published Specification DOS 1,768,623 and German Published Specification DAS 1,618,913.

It is particularly preferred to use the following oximes of the formula (III: 1-methylthioacetaldoxime, 1-butylthioacetaldoxime, 2-methyl-2-methylthiopropionaldoxime, diethyl 2-oximino-malonate, 2-oximino-1,3-dithiolane, 4-methyl-2-oximino-1,3-dithiolane, 2-oximino-1,3-oxathiolane, 2-oximino-1,3-dithiane, 2-oximino-1,3-oxathiane, 1-methylthio-glyoxylic acid methyl ester oxime and 1-methylthio-glyoxylic acid dimethylamide oxime.

The carbamic acid esters of the formula (V) are known and can be obtained by reacting the oximes of the formula (III) with methyl isocyanate.

All inert organic solvents can be used as diluents in the above-mentioned reactions for the preparation of the active compounds according to the invention. They include ethers such as diethyl ether, dioxane and tetrahydrofuran, hydrocarbons, such as benzene, and chlorinated hydrocarbons such as chloroform and chlorobenzene. To bind the hydrogen halide liberated in the reaction, a tertiary base such as triethylamine is preferably added to the reaction mixture. It is optionally also possible to start direct from the alkali metal salts of the oximes of the formula (III). Alternatively, it is possible to use all customary acid-binding agents to bind the hydrogen halides formed in the reaction, for example alkali metal carbonates, alkaline earth metal carbonates, alcoholates such as alkali metal methylate or ethylate, amines, alkali metal fluorides and alkaline earth metal fluorides.

The reaction temperatures can be varied over a fairly wide range; in general, the reaction is carried out at from 0° to 100° C, preferably at from 20° to 40° C.

In carrying out the process according to the invention, the starting compounds are generally employed in equimolar amounts. An excess of one or other starting compound is not disadvantageous, but also produces no significant increase in the yield of the compounds according to the invention.

The active compounds according to the invention display strong insecticidal, acaricidal and nematicidal effects while having a low toxicity to warm-blooded animals and low phytotoxicity. The active compounds can therefore be employed with good success for combating harmful sucking and biting insects and Diptera, including pests harmful to health and pests of stored products, mites and nematodes. Furthermore, they also have certain fungicidal and bacteriostatic effects.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*(, the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surina-

*mensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit-fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus telarius urticae*) and the European red mite (*Paratetranychus pilosus = Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the compounds of the present invention are also distinguished by an outstanding residual activity on wood and clay, as well as a good stability to alkali on limed substrates.

To the nematodes there belong, in the main, foliar nematodes (Aphelenchoides), such as the black-currant eelworm (*A. ritzemabosi*), the leaf-blotch eelworm (*A. fragariae*) and the rice eelworm (*A. oryzae*); stem nematodes (Ditylenchus), such as the stem eelworm (*D. dipsaci*); root-knot nematodes (Meloidogyne) such as *M. arenaria* and *M. incognita;* cystforming nematodes (Heterodera), such as the potato cyst eelworm (*H. rostochiensis*), and the beet cyst eelworm (*H. schachtii*); as well as free-living root nematodes, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, nematicides, fungicides and bactericides, or rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids, nematodes, fungi and bacteria, and more particularly methods of combating insects, acarids and nematodes, which comprises applying to at least one of correspondingly (a) such insects, (b) such acarids, (c) such nematodes, (d) such fungi, (e) such bacteria, and (f) the corresponding habitat thereof, i.e. the locus to be protected, e.g. to a growing crop, to an area where a crop is to be grown or to a domestic animal, a correspondingly combative or toxic amount, i.e. an insecticidally, acaricidally, nematicidally, fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

$LD_{100}$ test

Test insects: *Sitophilus granarius*

Solvent: Acetone

2 Parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per $m^2$ of filter-paper varied with the concentration of the solution of active compound. About 25 test insects were then placed in the Petri dish and it was covered with a glass lid.

The condition of the test insects was observed 3 days after the commencement of the experiments. The destruction, in %, was determined.

The active compounds, the concentrations of the active compounds and the results can be seen from the following table:

Table 1

| | $LD_{100}$ test | |
|---|---|---|
| Active Compounds | Active compound concentrations % strength of solution | Destruction in % |
| $CH_3S-\underset{\underset{CH_3}{\|}}{C}=N-O-CO-NH-CH_3$ (known) (A) | 0.2<br>0.02 | 90<br>0 |
| $CH_3S-\underset{\underset{CH_3}{\|}}{C}=N-O-CO-\underset{\underset{CH_3}{\|}}{N}-S-\langle\bigcirc\rangle$ (known) (B) | 0.2<br>0.02 | 90<br>0 |
| $CH_3-S-\underset{\underset{CH_3}{\|}}{\overset{\overset{CH_3}{\|}}{C}}-CH=NOCON-\underset{\underset{CH_3}{\|}}{}-S-\langle\bigcirc\rangle-CF_3$ (6) | 0.2<br>0.02 | 100<br>100 |
| $\underset{CH_3}{\overset{S}{\underset{S}{\diagup}}}\rangle=NOCON-\underset{\underset{CH_3}{\|}}{}-S-\langle\bigcirc\rangle-CF_3$ (5) | 0.2<br>0.02 | 100<br>100 |

EXAMPLE 2

$LT_{100}$ test for Diptera

Test Insects: *Musca domestica*

Solvent: Acetone

2 Parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction is determined.

The active compounds, the concentrations of the active compounds and the times at which there was 100% can be seen from the following table:

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm (e.g. mg/l), was decisive. The soil was filled into pots, lettuce was sown in and the pots were kept at a greenhouse temperature of 27° C. After 4 weeks, the lettuce roots were examined for infestation with nematodes, and the degree of effectiveness of the active compound was determined as a percentage. The degree of effectiveness was 100% when Table 2

$LT_{100}$ test for *Diptera*

| Active Compounds | | Active compound concentration of the solution in % | $LT_{100}$ |
|---|---|---|---|
| $CH_3S-\overset{\overset{CH_3}{\vert}}{C}=N-O-CO-\overset{\overset{CH_3}{\vert}}{N}-S-\text{\textlangle}\text{\textrangle}$ (known) | (B) | 0.2<br>0.02 | 95'<br>6 hrs. = 90% |
| $\overset{CH_3}{\underset{CH_3S}{\diagdown}}C=NOCON\overset{\overset{CH_3}{\vert}}{-}S-\text{\textlangle}\text{\textrangle}-CF_3$ | (1) | 0.2<br>0.02 | 85'<br>120' |
| $CH_3-S-\overset{\overset{CH_3}{\vert}}{\underset{\underset{CH_3}{\vert}}{C}}-CH=NOCON\overset{\overset{CH_3}{\vert}}{-}S-\text{\textlangle}\text{\textrangle}-CF_3$ | (6) | 0.2<br>0.02 | 55'<br>135' |
| $\begin{bmatrix}S\\S\end{bmatrix}=NOCON\overset{\overset{CH_3}{\vert}}{-}S-\text{\textlangle}\text{\textrangle}-CF_3$ | (4) | 0.2<br>0.02 | 100'<br>145' |
| $\begin{bmatrix}S\\S\end{bmatrix}=NOCON\overset{\overset{CH_3}{\vert}}{-}S-\text{\textlangle}\text{\textrangle}-CF_3$ (with $CH_3$) | (5) | 0.2<br>0.02 | 65'<br>160' |

EXAMPLE 3

Critical concentration test
Test nematode: *Meloidogyne incognita*
Solvent: 3 parts by weight of acetone
Emulsifier: 1 part by weight of alkylaryl polyglycol ether infestation was completely avoided; it was 0% when the infestation was exactly the same as in the case of the control plants in untreated soil which had been infested in the same manner.

The active compound, the amounts applied and the results can be seen from the following table:

Table 3

| | Critical concentration test | |
|---|---|---|
| | | Degree of destruction in % at active compound concentrations, in ppm, of |
| Active compound (structure) | | 20     10 |
| $CH_3S-\overset{\overset{CH_3}{\vert}}{C}=N-O-CO-\overset{\overset{CH_3}{\vert}}{N}-S-\text{\textlangle}\text{\textrangle}$ (known) (B) | | 0     0 |

Table 3-continued

Critical concentration test

| Active compound (structure) | Degree of destruction in % at active compound concentrations, in ppm, of | |
|---|---|---|
| | 20 | 10 |
| $CH_3\!-\!\underset{CH_3S}{\overset{}{C}}\!=\!NOCON\!-\!\underset{CH_3}{\overset{}{N}}\!-\!S\!-\!C_6H_4\!-\!CF_3$  (1) | 100 | 95 |
| (dithiolane)$=\!NOCON(CH_3)\!-\!S\!-\!C_6H_4\!-\!CF_3$  (4) | 100 | 100 |
| (methyl-dithiolane)$=\!NOCON(CH_3)\!-\!S\!-\!C_6H_4\!-\!CF_3$  (5) | 100 | 100 |
| $CH_3\!-\!S\!-\!C(CH_3)_2\!-\!CH\!=\!NOCON(CH_3)\!-\!S\!-\!C_6H_4\!-\!CF_3$  (6) | 100 | 100 |

EXAMPLE 4

Hyponomeuta test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier and the concentrate was diluted with water to the desired concentration.

Leaves of apple trees were sprayed with the preparation of active compound until dew-moist and caterpillars of the small ermine moth (*Hyponomeuta padella*) were placed on the leaves.

After the stated times, the degree of destruction in % was determined. 100% denotes that all of the caterpillars had been killed, whereas 0% indicates that no caterpillars had been killed.

The active compounds, active-compound concentrations, evaluation times and results can be seen from the table which follows:

Table 4

(Insects which damage plants)
*Hyponomeuta* test

| Active compounds | Active compound concentration in % | Degree of destruction in % after 3 days |
|---|---|---|
| $CH_3S\!-\!\underset{\phantom{CH_3}}{\overset{CH_3}{C}}\!=\!N\!-\!O\!-\!CO\!-\!NH\!-\!CH_3$ (known)  (A) | 0.02<br>0.004 | 15<br>0 |

Table 4-continued (Insects which damage plants)
*Hyponomeuta* test

| Active compounds | Active compound concentration in % | Degree of destruction in % after 3 days |
|---|---|---|
| $CH_3\!-\!\underset{CH_3S}{\overset{}{C}}\!=\!NOCON(CH_3)\!-\!S\!-\!C_6H_4\!-\!CF_3$  (1) | 0.02<br>0.004 | 80<br>60 |

EXAMPLE 5

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 5

(Insects which damage plants)
*Myzus* test

| Active compounds | Active compound concentration in % | Degree of destruction in % after 1 day |
|---|---|---|
| CH₃S—C(CH₃)=N—O—CO—NH—CH₃  (known) (A) | 0.01<br>0.001 | 100<br>20 |
| CH₃S—C(CH₃)=N—O—CO—N(CH₃)—S—C₆H₅  (known) (B) | 0.01<br>0.001 | 90<br>0 |
| CH₃S—C(CH₃)₂—CH=N—O—CO—N(CH₃)—S—C₆H₄—CF₃  (6) | 0.01<br>0.001 | 100<br>90 |
| [dithiolane]=N—O—CO—N(CH₃)—S—C₆H₄—CF₃  (4) | 0.01<br>0.001 | 100<br>80 |
| [methyl-dithiolane]=N—O—CO—N(CH₃)—S—C₆H₄—CF₃  (5) | 0.01<br>0.001 | 100<br>100 |

EXAMPLE 6

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed, whereas 0% means that none of the spider mites were killed.

The active compounds, the concentrations of the active compounds, the evaluation times and the results can be seen from the following table:

Table 6

(Mites which damage plants)
*Tetranychus* test

| Active compounds | Active compound concentration in % | Degree of destruction in % after 2 days |
|---|---|---|
| CH₃S—C(CH₃)=N—O—CO—NH—CH₃  (known) (A) | 0.1<br>0.01 | 98<br>0 |
| CH₃S—C(CH₃)=N—O—CO—N(CH₃)—S—C₆H₅  (known) (B) | 0.1<br>0.01 | 75<br>0 |
| CH₃S—C(CH₃)₂—CH=N—O—CO—N(CH₃)—S—C₆H₄—CF₃  (6) | 0.1<br>0.01 | 98<br>80 |

The process of this invention is illustrated by the following preparative Example.

EXAMPLE 7

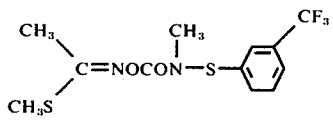 (1)

12.7 g of N-methyl-N-(3-trifluoromethylphenyl sulfenyl)carbamic acid fluoride and 5.3 g of 1-methylthioacetaldoxime were dissolved in 200 ml of toluene. 6 g of triethylamine were then added dropwise, while stirring. In the course thereof, the temperature was not permitted to rise above 40° C. The mixture was stirred for a further 3 hours at room temperature. The amine hydrofluoride was then filtered off and the solution was repeatedly extracted by shaking with cold water. After drying, the solvent was distilled off. An oil remained having a refractive index $n_D^{20}$ of 1.5388. Yield: 12 g (71%).

The following were prepared analogously:

(2) $n_D^{20}$: 1.5012

(3) $n_D^{20}$: 1.5250

(4) melting point 107–109° C (5) $n_D^{20}$: 1.5553

(6) $n_D^{20}$: 1.5212

(7) viscous oil (8) melting point 66° C (9) viscous oil

Other active compounds which can be produced as above include:

(10)

(11)

(12)

(13)

(14)

(15)

(16)

(17)

(18)

(19)

(20)

(21)

-continued

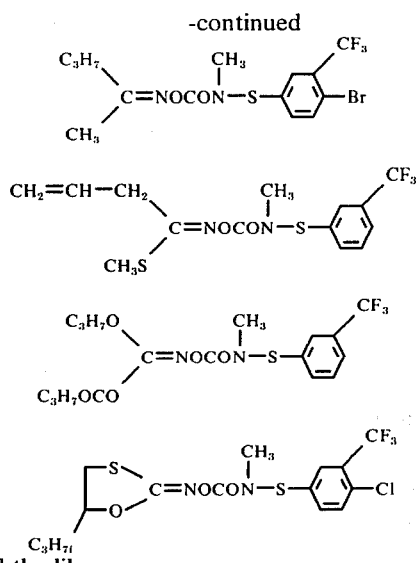

and the like.

It will be appreciated that the instant specification and examples are set forth by way of illustration and not limitation, and that various modifications and changes may be made without departing from the spirit and scope of the present invention.

What is claimed is:

1. An N-sulfenylated oxime-carbamate of the formula

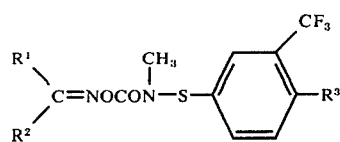

in which

R¹ and R² each independently is hydrogen, alkyl, alkenyl, alkynyl, alkoxy, alkylthio, alkoxycarbonyl, aminocarbonyl or alkylthioalkyl, R³ is hydrogen or halogen.

2. A compound according to claim 1, in which R¹ is hydrogen, straight-chain or branched alkyl with 1–4 carbon atoms, alkylthio with 1–4 carbon atoms, alkoxycarbonyl with 1–4 carbon atoms in the alkyl moiety, dialkylaminocarbonyl with 1–4 carbon atoms in each alkyl moiety, or alkylthioalkyl with up to 4 carbon atoms in each alkyl moiety, and R₂ is alkylthio with 1–4 carbon atoms or alkylthioalkyl with 1–4 carbon atoms in each alkyl moiety.

3. The compound according to claim 1 wherein such compound is N-methyl-N-(3-trifluoromethylphenylsulfenyl)1-methylthioacetaldoxime-carbamate of the formula

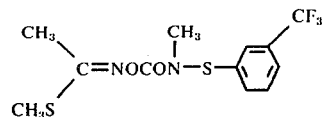

4. The compound according to claim 1 wherein such compound is N-methyl-N-(3-trifluoromethylphenylsulfenyl)-2-methyl-2-methylthiopropionaldoxime-carbamate of the formula

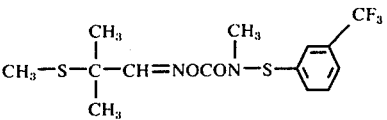

5. The compound according to claim 1 wherein such compound is N-methyl-N-(3-trifluoromethylphenylsulfenyl)-1-methylthioglyoxylic acid dimethylamide oxime-carbamate of the formula

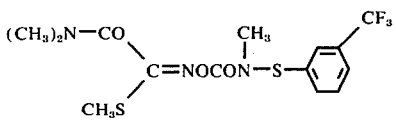

6. An insecticidal, acaricidal, nematicidal, fungicidal or bactericidal composition containing as active ingredient an insecticidally, acaricidally, nematicidally, fungicidally or bactericidally effective amount of a compound according to claim 1 in admixture with a diluent.

7. A method of combating insects, acarids, nematodes, fungi or bacteria which comprises applying to the insects, acarids, nematodes, fungi or bacteria or to a habitat thereof an insecticidally, acaricidally, nematicidally, fungicidally or bactericidally effective amount of a compound according to claim 1.

8. The method according to claim 7 in which said compound is
N-methyl-N-(3-trifluoromethylphenylsulfenyl)-1-methylthioacetaldoxime-carbamate,
1,3-thiolane-2-oximino-carbamate,
N-methyl-N-(3-trifluoromethylphenylsulfenyl)
N-methyl-N-(3-trifluoromethylphenylsulfenyl)-2-methyl-2-methylthiopropionaldoxime-carbamate, or
N-methyl-N-(3-trifluoromethylphenylsulfenyl)-1-methylthioglyoxylic acid dimethylamide oximecarbamate.

* * * * *

UNITED STATES PATENT AND TRADEMARK OFFICE
CERTIFICATE OF CORRECTION

PATENT NO. : 4,008,328
DATED : February 15, 1977
INVENTOR(S) : Peter Siegle et al It is certified that error appears in the above-identified patent and that said Letters Patent are hereby corrected as shown below:

Claim 8, col. 18, lines 46 & 47     delete "1,3-thiolane-2-oximino-carbamate, N-methyl-N-(3-trifluoromethylphenylsulfenyl)"

Col. 1, line 58     cancel "shain" and substitute -- chain --

Claim 8, line 52     cancel "oximecarbamate" and substitute -- oxime-carbamate --

Signed and Sealed this

Eleventh Day of October 1977

[SEAL]

Attest:

RUTH C. MASON
Attesting Officer

LUTRELLE F. PARKER
Acting Commissioner of Patents and Trademarks